(12) United States Patent
Webb et al.

(10) Patent No.: US 6,329,500 B1
(45) Date of Patent: Dec. 11, 2001

(54) TRANSFORMING GROWTH FACTOR-β BINDING SITE

(75) Inventors: Donna J. Webb; Steven L. Gonias, both of Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/311,352

(22) Filed: May 13, 1999

Related U.S. Application Data

(60) Provisional application No. 60/085,574, filed on May 15, 1998.

(51) Int. Cl.[7] .......................... C07K 7/06; C07K 14/435; A61K 38/08; A61K 38/17

(52) U.S. Cl. .......................... 530/328; 530/300; 530/350; 530/827; 530/829; 514/2

(58) Field of Search ..................................... 530/300, 350, 530/328, 827, 829; 514/2

(56) References Cited

PUBLICATIONS

LaMarre, J. et al. A alpha 2–macroglobulin receptor–dependent mechanism for the plasma clearance of transforming growth factor–beta 1 in mice. J. Clin. Invest. 87(1): 39–44, Abstract only. Jan. 1991.*

Lysiak, J.J. et al. Alpha 2–macroglobulin functions as a cytokine carrier to induce nitric oxide synthesis and cause nitric oxide–dependent cytotoxicity in the RAW 264.7 macrophage cell line. J. Biol. Chem. 270(37): 21919–21927, Sep. 1995.*

Webb, D.J. et al. Localization of the binding site for transforming growth factor–beta in human alpha 2–macroglobulin to a 20–kDa peptide that also contains the bait region. J. Biol. Chem. 273(21): 13339–13346, May 1998.*

* cited by examiner

Primary Examiner—Anthony C. Caputa
Assistant Examiner—Anne L. Holleran
(74) Attorney, Agent, or Firm—John P. Breen

(57) ABSTRACT

The present invention relates to a composition and method for inhibiting TGF-β activity. The composition comprises a TGF-β neutralizing peptide derived from $\alpha_2$-macroglobulin that binds to TGF-β and inhibits TGF-β activity.

5 Claims, 9 Drawing Sheets

SEQUENCE LISTING

<160> NUMBER OF SEQ ID NOS: 6

<210> SEQ ID NO 1
<211> LENGTH: 339
<212> TYPE: DNA
<213> ORGANISM: Homo sapiens

<400> SEQUENCE: 1

```
ggacctgaag gtctacgtgt aggtttttat gagtcagatg taatgggaag aggccatgca    60
cgcctggtgc atgttgaaga gcctcacacg gagaccgtac gaaagtactt ccctgagaca   120
tggatctggg atttggtggt ggtaaactca gcagggtgg ctgaggtagg agtaacagtc   180
cctgacacca tcaccgagtg gaaggcaggg gccttctgcc tgtctgaaga tgctggactt   240
ggtatctctt ccactgcctc tctccgagcc ttccagcccc tctttgtgga gctcacaatg   300
ccttactctg tgattcgtgg agaggccttc acactcaag                          339
```

<210> SEQ ID NO 2
<211> LENGTH: 113
<212> TYPE: PRT
<213> ORGANISM: Homo sapiens

<400> SEQUENCE: 2

```
Gly Pro Glu Gly Leu Arg Val Gly Phe Tyr Glu Ser Asp Val Met Gly
 1               5                  10                  15

Arg Gly His Ala Arg Leu Val His Val Glu Glu Pro His Thr Glu Thr
                20                  25                  30

Val Arg Lys Tyr Phe Pro Glu Thr Trp Ile Trp Asp Leu Val Val Val
            35                  40                  45

Asn Ser Ala Gly Val Ala Glu Val Gly Val Thr Val Pro Asp Thr Ile
        50                  55                  60

Thr Glu Trp Lys Ala Gly Ala Phe Cys Leu Ser Glu Asp Ala Gly Leu
    65                  70                  75                  80

Gly Ile Ser Ser Thr Ala Ser Leu Arg Ala Phe Gln Pro Phe Phe Val
                85                  90                  95

Glu Leu Thr Met Pro Tyr Ser Val Ile Arg Gly Glu Ala Phe Thr Leu
               100                 105                 110
Lys
```

<210> SEQ ID NO 3
<211> LENGTH: 549
<212> TYPE: DNA
<213> ORGANISM: Homo sapiens

<400> SEQUENCE: 3

```
tcggcgtcct cggtttacaa cctgctacca gaaaaggacc tcactggctt ccctgggcct    60
ttgaatgacc aggacgatga agactgcatc aatcgtcata atgtctatat taatggaatc   120
acatatactc cagtatcaag tacaaatgaa aaggatatgt acagcttcct agaggacatg   180
```

```
ggcttaaagg cattcaccaa ctcaaagatt cgtaaaccca aaatgtgtcc acagcttcaa      240
cagtatgaaa tgcatggacc tgaaggtcta cgtgtaggtt tttatgagtc agatgtaatg      300
ggaagaggcc atgcacgcct ggtgcatgtt gaagagcctc acacggagac cgtacgaaag      360
tacttccctg agacatggat ctgggatttg gtggtggtaa actcagcagg ggtggctgag      420
gtaggagtaa cagtccctga caccatcacc gagtggaagg cagggggcctt ctgcctgtct     480 gaagatgctg gacttggtat ctcttccact gcctctctcc gagccttcca gcccttcttt      540
gtggagctc                                                              549
```

<210> SEQ ID NO 4
<211> LENGTH: 183
<212> TYPE: PRT
<213> ORGANISM: Homo sapiens

<400> SEQUENCE: 4

```
Ser Ala Ser Ser Val Tyr Asn Leu Leu Pro Glu Lys Asp Leu Thr Gly
  1               5                  10                  15

Phe Pro Gly Pro Leu Asn Asp Gln Asp Asp Glu Asp Cys Ile Asn Arg
             20                  25                  30

His Asn Val Tyr Ile Asn Gly Ile Thr Tyr Thr Pro Val Ser Ser Thr
         35                  40                  45

Asn Glu Lys Asp Met Tyr Ser Phe Leu Glu Asp Met Gly Leu Lys Ala
     50                  55                  60

Phe Thr Asn Ser Lys Ile Arg Lys Pro Lys Met Cys Pro Gln Leu Gln
 65                  70                  75                  80

Gln Tyr Glu Met His Gly Pro Gly Leu Arg Val Gly Phe Tyr Glu
                 85                  90                  95

Ser Asp Val Met Gly Arg Gly His Ala Arg Leu Val His Val Glu Glu
                100                 105                 110

Pro His Thr Glu Thr Val Arg Lys Tyr Phe Pro Glu Thr Trp Ile Trp
                115                 120                 125

Asp Leu Val Val Val Asn Ser Ala Gly Val Ala Glu Val Gly Val Thr
            130                 135                 140

Val Pro Asp Thr Ile Thr Glu Trp Lys Ala Gly Ala Phe Cys Leu Ser
145                 150                 155                 160

Glu Asp Ala Gly Leu Gly Ile Ser Ser Thr Ala Ser Leu Arg Ala Phe
                165                 170                 175

Gln Pro Phe Phe Val Glu Leu
            180
```

<210> SEQ ID NO 5
<211> LENGTH: 28
<212> TYPE: DNA
<213> ORGANISM: Homo sapiens

<400> SEQUENCE: 5

```
tggccttaag tgtgaaggcc tctccacg                                          28
```

<210> SEQ ID NO 6
<211> LENGTH: 28
<212> TYPE: DNA
<213> ORGANISM: Homo sapiens

<400> SEQUENCE: 6

```
gcatggatcc gaaggtctac gtgtaggt                                          28
```

TRANSFORMING GROWTH FACTOR-β BINDING SITE

CLAIM TO PRIORITY

This application claims priority under 35 USC §119(e) to U.S. Provisional Application Serial No. 60/085,574, filed May 15, 1998.

U.S. GOVERNMENT RIGHTS

This invention was made with United States Government support under Grant No. CA-53462, awarded by National Institutes of Health. The United States Government has certain rights in the invention.

FIELD OF THE INVENTION

The present invention is directed to a therapeutic peptide and compositions thereof, nucleic acid sequences encoding the peptide and a method for inhibiting cytokine activity in a patient by administering a composition comprising the peptide. More particularly the present invention is directed to inhibiting TGF-β activity by administering a peptide having the TGF-β binding domain of $\alpha_2$-macroglobulin.

BACKGROUND OF THE INVENTION

Human $\alpha_2$-macroglobulin ($\alpha_2$M) is a 718-kDa glycoprotein that was originally characterized as a broad-spectrum proteinase inhibitor. More recent experiments have demonstrated that ($\alpha_2$-Macroglobulin ($\alpha_2$M) also binds and regulates the activity of various cytokines, see Gonias, Exp. Hematol. 20:302–311 (1992). The structure of $\alpha_2$M consists of four identical subunits, each with 1451 amino acids. The subunits are linked into dimers by disulfide bonds and into intact homotetramers by noncovalent interactions.

Proteinases react with $\alpha_2$M by cleaving any of a number of susceptible peptide bonds in the "bait region", which includes amino acids 666–706. Bait region cleavage causes $\alpha_2$M to undergo a major conformational change, which effectively "traps" the attacking proteinase in a complex which is non-dissociable, even when the proteinase and the inhibitor are not covalently linked. Conformational change also reveals binding sites for the $\alpha_2$M receptor/low density-lipoprotein receptor-related protein (LRP). These binding sites have been localized to 18-kDa peptides at the C-terminus of each $\alpha_2$M subunit; Lys-1370 and Lys-1374 play particularly important roles.

Like the complement components, C3 and C4, each $\alpha_2$M subunit contains a novel thiol ester bond, which is formed from the side-chains of Cys-949 and Glu-952, and these thiol esters may be instrumental in determining the conformational state of $\alpha_2$M. When $\alpha_2$M reacts with a proteinase, the thiol esters emerge from within hydrophobic, solvent-restricted clefts and are cleaved by nucleophiles or $H_2O$. Small primary amines, such as methylamine, penetrate the hydrophobic clefts and react with $\alpha_2$M thiol esters independently of proteinases, inducing an equivalent or nearly equivalent conformational change.

In addition to its activity as a proteinase inhibitor, $\alpha_2$M functions as a major carrier and regulator of certain cytokines, including isoforms of the transforming growth factor-β (TGF-β) family. The highest affinity interactions of $\alpha_2$M involve members of the transforming growth factor-β (TGF-β) and neurotorphin families. O'Connor-McCourt and Wakefield first identified $\alpha_2$M as a physiologically significant carrier of TGF-β in human serum (J. Biol. Chem. 262, 14090–14099, 1987). Their studies demonstrated that nearly all of the TGF-β1 in serum is associated with $\alpha_2$M and that the bound TGF-β1 is inactive. Huang et al. (J. Biol. Chem. 263, 1535–1541, 1988) confirmed the role of $\alpha_2$M as a TGF-β-carrier and demonstrated that the TGF-β-binding activity of $\alpha_2$M depends on its conformational state.

More recent studies have demonstrated the function of $\alpha_2$M as a TGF-β-carrier in animal model systems. When radioiodinated TGF-β1 is injected intravascularly in mice, the cytokine is cleared rapidly at first; however, this is followed by a slow-clearance phase, during which time the TGF-β is almost entirely $\alpha_2$M-associated.

The TGF-β family of cytokines regulates diverse processes including cellular growth, differentiation, wound healing, and inflammation. At the cellular level, TGF-β response is mediated by or regulated by a variety of receptors and binding proteins, including the type I and type II receptors, which are serine/threonine kinases, betaglycan, and endoglin. TGF-β activity is also regulated by processes that alter delivery of the active cytokine to the cell surface. For example, TGF-β is secreted as a large latent complex that includes the propeptide, latency associated peptide (LAP), and a second gene product, latent TGF-β-binding protein (LTBP). Conversion of latent TGF-β into active 25-kDa homodimer requires dissociation of LAP and LTBP in reactions which may be mediated by proteinases, thrombospondin, the mannose 6-phosphate/insulin-like growth factor-II receptor and acidic microenvironments. Once activated, the 25-kDa form of TGF-β may bind to $\alpha_2$M, once again forming a complex that is unavailable for receptor-binding.

Binding of TGF-β to $\alpha_2$M is initially non-covalent and reversible; however, the complex can become covalently stabilized as a result of thiol-disulfide exchange. The latter reaction is observed primarily with conformationally-altered $\alpha_2$M, since native $\alpha_2$M lacks free thiol groups. A number of complementary methods have been used to determine equilibrium dissociation constants ($K_D$) for the interaction of TGF-β with $\alpha_2$M (Arch. Biochem. Biophys. 292,487–49, 1992;J. Biol. Chem. 269,1533–1540, 1994; and Ann. N. Y. Acad. Sci. USA 737,273–290, 1994). The $K_D$s for the binding of TGF-β1 and TGF-β2 to native $\alpha_2$M are 300 nNM and 10 nM, respectively; the $K_D$s for the binding of TGF-β1 and TGF-β2 to methylamine-modified $\alpha_2$M ($\alpha_2$M-MA) are 80 nM and 10 nM, respectively. These binding constants accurately predict the ability of $\alpha_2$M to neutralize TGF-β in cell culture systems.

In cell culture systems, $\alpha_2$M neutralizes both exogenously-added and endogenously-synthesized TGF-β. Neutralization of endogenously-synthesized TGF-β results in altered gene expression, including greatly increased expression of inducible nitric oxide synthase (iNOS) by murine macrophages and increased expression of platelet-derived growth factor α-receptor by vascular smooth muscle cells (see J. Biol. Chem. 270, 21919–21927, 1995 and J. Biol. Chem. 270, 30741–30748, 1995). $\alpha_2$M gene knock-out mice demonstrate increased tolerance to endotoxin challenge and this characteristic is most likely explained by the enhanced function of TGF-β as an immunosuppressive, in the absence of $\alpha_2$M.

The fate of $\alpha_2$M-associated TGF-β depends on the $\alpha_2$M conformation. Native $\alpha_2$M, which is the predominant form of $\alpha_2$M present in the plasma and probably in most extravascular microenvironments, binds TGF-β reversibly and non-covalently. Thus, native $\alpha_2$M may buffer tissues against rapid changes in TGF-β levels by binding or slowly releasing the cytokine in response to the free TGF-β concentration. Based on the $K_D$ value, it is believed that approximately 95% of the TGF-β1 in plasma is $\alpha_2$M-associated under equilibrium conditions, even though TGF-β1 binds to native $\alpha_2$M with lower affinity than TGF-β2. Conversion of $\alpha_2$M into the transformed conformation, which probably occurs most frequently at sites of inflammation due to the increase in cellular proteinase secretion, alters the mechanisms by which TGF-β is regulated. First, transformed $\alpha_2$M has free Cys residues and thus undergoes thiol-disulfide exchange with TGF-β, eliminating the potential for release of active cytokine. Second, $\alpha_2$M-proteinase complexes bind to the endocytic receptor, LRP; bound TGF-β is internalized with the $\alpha_2$M-proteinase complex and probably delivered to lysosomes.

The mechanism by which $\alpha_2$M binds cytokines remains unclear. Early studies, suggesting a prominent role for the thiol ester-derived Cys-residues, were not confirmed for TGF-β1 and TGF-β2. When $\alpha_2$M-MA was treated with papain to release the 18-kDa receptor binding domains, the TGF-β-binding activity remained with the residual 600-kDa $\alpha_2$M fragment. Thus, the cytokine- and LRP-binding sites are not co-localized. One proposed mechanism for $\alpha_2$M binding was that the central cavity in the structure of $\alpha_2$M, which serves as the proteinase-trap, also non-specifically binds cytokines. Arguments in support of the this model include: the complex quaternary structure of $\alpha_2$M, the known trapping mechanism by which $\alpha_2$M interacts with proteinases, and the large number of structurally unrelated cytokines which have been reported to associate with $\alpha_2$M. In accordance with the present invention the TGF-β-binding domain has now been localized to a specific region in the structure of human $\alpha_2$M.

SUMMARY OF THE INVENTION

The present invention is directed to the identification of the $\alpha_2$M binding domain for TGF-β and the use of that binding domain to formulate compositions for treating conditions relating to excess TGF-β activity. More particularly, a composition and method for inhibiting TGF-β activity in vivo and treating a pathologic condition caused by, or resulting from TGF-β activity is described. The composition comprises a TGF-β neutralizing peptide and a pharmaceutically acceptable carrier and the method comprises the step of administering the composition to a patient in need of such therapy.

DETAILED DESCRIPTION OF THE INVENTION

Figure 1:
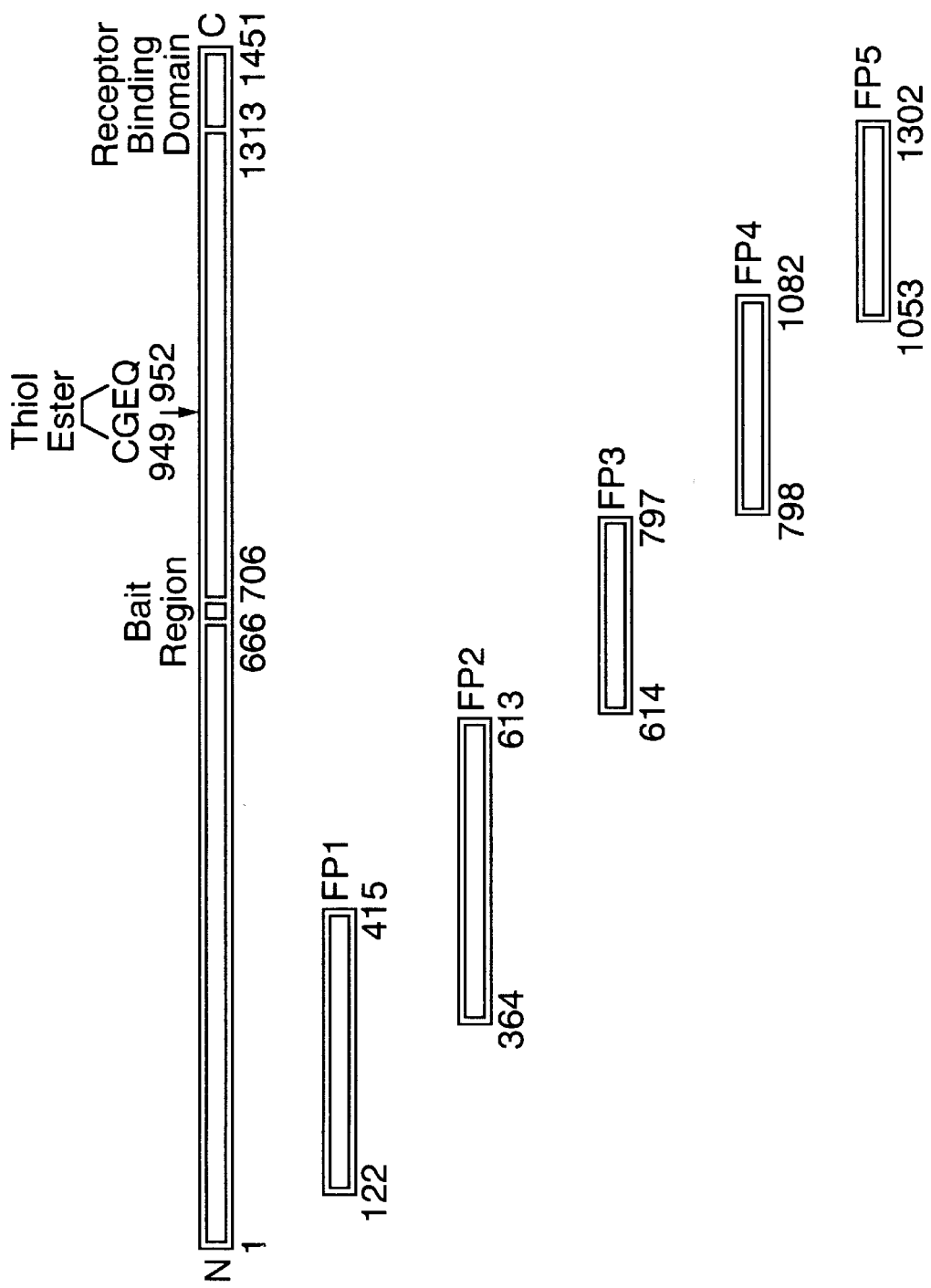
FIG. 1. Schematic representation of the $\alpha_2$M subunit and the $\alpha_2$M peptides which were incorporated into GST-fusion proteins. The amino acid numbering is based on the structure of the mature $\alpha_2$M subunit.

In describing and claiming the invention, the following terminology will be used in accordance with the definitions set forth below.

As used herein, the term "purified" means that the molecule or compound is substantially free of contaminants normally associated with the molecule or compound in a native or natural environment.

Transforming growth factor-β (TGF-β) refers to a family of multi-functional cell regulatory factors produced in various forms by many cell types (for review see Spom et al,. J. Cell Biol., 105: 1039 (1987)). Five distinct isoforms of TGF-β have been identified TGF-$\beta_{1-5}$ and the gerneral term TGF-β is intended to include all isoforms of TGF-β.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, "effective amount" means an amount sufficient to produce a selected effect. For example, an effective amount of a TGF-β neutralizing peptide is an amount of the peptide sufficient to reduce TGF-β activity or modify TGF-β activity. A "therapeutic effective amount" is an amount of the peptide sufficient to reduce the symptoms associated with excess TGF-β activity.

The invention also encompasses nucleic acid molecules and peptides which differ from actual nucleic acid and peptide molecules shown in the Sequence Listing, but which produce the same phenotypic effect. These altered, but phenotypically equivalent nucleic acid and peptide molecules are referred to as "equivalent nucleic acids" and "equivalent peptides", respectively. This invention also encompasses nucleic acid molecules characterized by changes in non-coding regions that do not alter the phenotype of the polypeptide produced therefrom when compared to the nucleic acid molecule of the present invention. As used herein, the term "nucleic acid" encompasses RNA as well as single and double-stranded DNA and cDNA.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$–C$_4$ alkyl;

2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or C$_1$–C$_4$ alkyl with the proviso that R and R$_1$ are not both hydrogen;

3. peptides wherein the C terminus is derivatized to —C(O)R$_2$ where R$_2$ is selected from the group consisting of C$_1$–C$_4$ alkoxy, and —NR$_3$R$_4$ where R$_3$ and R$_4$ are independently selected from the group consisting of hydrogen and C$_1$–C$_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gln or Q; Asparagine is Ash or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, gentically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

The TGF-β family of cytokines regulates diverse processes including cellular growth, differentiation, wound healing, and inflammation. Notwithstanding the beneficial and essential cell regulatory functions provided by TGF-β activity, TGF-β activity can be detrimental to its host organism. For example, while TGF-β induced growth and proliferation of mesenchymal cells is typically desirable, some tumor cells may also be stimulated by TGF-β activity. In addition, it is anticipated that neutralizing TGF-β activity may enhance localized immune response to tumors. Accordingly, the use of inhibitors of TGF-β activity can be used to treat cancer.

TGF-β activity is also normally present at the site of tissue damage and the stimulation of extracellular matrix production by TGF-β is essential for wound healing. However, in some cases, the TGF-β response is uncontrolled and an excessive accumulation of extracellular matrix results. An example of excessive accumulation of extracellular matrix is glomerulonephritis and scar tissue formation. Furthermore, it is thought that diseases characterized by inflamation such as Psoriasis are aggravated by TGF-β activity. Additional examples of TGF-β aggravated pathologies may include rheumatoid arthritis and atherosclerosis. Each of these conditions can be treated with the peptide compositions of the present invention to alleviate the pathological associated symptoms.

As used herein, "pathologic conditions" refers to any pathology arising by or aggravated by TGF-β activity. These include conditions caused by or aggravated by inflammation, for example, rheumatoid arthritis, inflamed skin lesions, scar tissue formation, lung fibrosis, liver fibrosis, atherosclerosis, psoriasis or glomerulonephritis.

The present invention provides a method of modifying a biological function mediated by the regulatory activity of TGF-β. The method comprises administering an effective amount of a TGF-β neutralizing peptide. As used herein, "a TGF-β neutralizing peptide" refers to a peptide or peptide mimetic that binds to TGF-β and prevents or inhibits TGF-β activity. Examples of TGF-β activity include, but are not limited to the stimulation of cell proliferation, stimulation of inflamation, inhibition of the immune response, and promotion of extracellular matrix proteins.

In one embodiment TGF-β activity is inhibited by contact with a peptide or peptide frament of SEQ ID NO: 2 or SEQ ID NO: 4. The method can be practiced in vitro or in vivo. If the method is practiced in vitro, a biological sample containing TGF-β is contacted directly with the peptide, peptide mimetic or pharmaceutical composition of the present invention. In one preferred embodiment the inhibition of TGF-β is effected in vivo by administering a polypeptide, a protein or a pharmaceutical composition, to a vertebrate species, and more preferably a mammalian species and typically a human patient.

In accordance with one embodiment a composition is provided for inhibiting TGF-β activity. The composition comprises a TGF-β neutralizing peptide fragment or mimetic peptide isolated/derived from $\alpha_2$-macroglobulin wherein the peptide contains the binding domain for TGF-β. The peptides or peptide mimetics can be recombinantly derived, chemically synthesized or isolated/purified from native sources. In one embodiment the composition comprises a substantially pure peptide fragment of SEQ ID NO: 2 or SEQ ID NO: 4, wherein the peptide retains the ability to bind to TGF-β. In one embodiment the neutralizing peptide is SEQ ID NO: 2.

The peptide or peptide mimetic compositions of the present invention are used to treat disease states that are caused by or aggravated by TGF-β activity. The method comprises the step of administering the composition in a form that contacts TGF-β with the neutralizing peptide fragment (or mimetic peptide) in an amount effective to reduce the activity of TGF-β. It is anticipated that the present compositions will be effective for treating psoriasis, cancer, rheumatoid arthritis, inflamed skin lesions, scar tissue formation, lung fibrosis, liver fibrosis, atherosclerosis or glomerulonephritis.

In one embodiment a patient having a condition aggravated by TGF-β activity is treated by administering a composition comprising the TGF-β neutralizing peptide fragment (or mimetic peptide) and a pharmaceutically acceptable carrier. In one embodiment the TGF-β neutralizing peptide, or peptide mimetic thereof, comprising a 20 amino acid sequence identical to any 20 consecutive amino acids of SEQ ID NO: 2 or SEQ ID NO: 4, and more preferably a peptide, or peptide mimetic thereof, comprising a 10 amino acid sequence identical to any 10 consecutive amino acids of SEQ ID NO: 2 or SEQ ID NO: 4.

Methods of administration are well known to those of skill in the art and include, but are not limited to oral, parenteral or topical administration. More particularly, oral dosage forms of the TGF-β neutralizing peptides, or peptide mimetics thereof, can be administered in the form of tablets, capsules, sugar- or film-coated tablets, liquid solutions or suspensions. Dosage forms for parenteral administration, for example intramuscular, intravenous or subcutaneous administration can be formulated in physiological saline using techniques known to those skilled in the art. The composition of the present invention can also be formulated as an ointment, cream, gel, lotions, foams and sprays for topical administration, or the composition can be formulated for delivery by a dermal patch using standard techniques known to those skilled in the art. The route of administration is determined in part by the pathological condition to be treated. In accordance with one embodiment the composition is administered intravenously and the condition to be treated is cancer.

Administration can be effected continuously or intermittently such that the amount is effective for its intended purpose. The dosage depends on a variety of factors including the age, weight and condition of the patient and the route of administration.

Nucleic acid sequences encoding the peptides of the present invention are also within the scope of the present invention. In accordance with one embodiment an isolated nucleic acid sequence comprising the sequence of SEQ ID NO: 1 is provided. That nucleic acid sequence can be operably linked to eukaryotic or prokaryotic regulatory sequences to allow for expression of the gene product which is a TGF-β neutralizing peptide. Accordingly, vectors comprising DNA sequences encoding the peptides of the present invention, adapted for expression in a bacterial cell, a yeast cell, a mammalian cell and other animal cells are also within the scope of the present invention. Expression vectors comprising the regulatory elements necessary for expression of the DNA in the bacterial, yeast, mammalian or animal cells are commercially available and can be used to operably link host cell expression regulatory sequences to the DNA sequence encoding the peptide. Regulatory elements required for expression include promoter sequences to bind RNA polymerase and transcription initiation sequences for ribosome binding that are well known to the skilled practitioner.

The present invention also includes the recombinant prokaryotic or eukaryotic cells transformed with the nucleic acid sequences of the present invention. An example of a suitable host cells for use in accordance with the present invention include the prokaryotic organism *E. coli* and eukaryotic yeast cells such as those organisms selected from the genus Saccromyces. In addition, various mammalian cells may be utilized as hosts, including, for example, mouse fibroblast cell NIH3T3, CHO cells, HeLa cells, Ltk-cells, etc. Expression vectors can be used to transfect the host cells by methods well known in the art such as calcium phosphate precipitation, DEAE-dextran, electroporation or microinjection.

EXAMPLE 1

Localization of the $\alpha_2$-macroglobulin Binding Site to the FP3 Peptide Fragment Materials and Methods Reagents and Proteins TGF-β2 was purchased from Genzyme (Cambridge, Mass.). TGF-β1 was from R&D Systems (Minneapolis, Minn.). Nerve growth factor-β (NGF-β) was purified from male mouse submaxillary glands by the method of Darling and Shooter, *Methods for Serum-Free Culture of Neuronal and Lymphoid Cells* (Barnes, D. W., Sirbasku, D. A., and Sato, G. H., Eds.) Vol. 4, pp. 79–83, Alan R. Liss, Inc., New York (1984). Methylamine HCl, chloramine T, iodoacetamide (IAM), dithiothreitol (DTT), isopropylthio-β-D-galactoside (IPTG), N-octyl glucopyranoside, glutathione S-transferase (GST), glutathione, anti-GST IgG fraction of antiserum, and bovine serum albumin (BSA) were from Sigma. $Na^{125}I$ was from Amersham (Arlington Heights, Ill.). pGEX-3X, pGEX-2T, and prepacked glutathione-Sepharose-4B columns were from Pharmacia. Immulon 2 microtiter plates were from Dynatech Laboratories (Chantilly, Va.). Polyvinylidene fluoride (PVDF) and nitrocellulose membranes were from Millipore. Iodogen was from Pierce (Rockford, Ill.). RPMI 1640, Dulbecco's modified Eagle's medium (DMEM), and Trypsin-EDTA were from Life Technologies, Inc. Fetal bovine serum (FBS) was from Hyclone Laboratories. Acidic fibroblast growth factor and basic fibroblast growth factor were from Promega.

$\alpha$-Macroglobulins and Related Derivatives

Human $\alpha_2M$ was purified from plasma by the method of Imber and Pizzo *J. Biol. Chem.* 256, 8134–8139 (1981). Murinoglobulin (MUG) was purified from the plasma of CD-1 female mice as previously described *J. Biol. Chem.* 271, 24982–24988 (1996). SDS-PAGE analysis of purified MUG revealed a single band with an apparent mass of 180 kDa. $\alpha_2$M-MA was prepared by dialyzing human $\alpha_2M$ against 200 mM methylamine-HCl in 50 mM Tris-HCl, pH 8.2 for 12 h at 22° C. followed by extensive dialysis against 20 mM sodium phosphate, 150 mM NaCl, pH 7.4 (PBS) at 4° C. Complete modification of native $\alpha_2M$ by methylamine was confirmed by loss of trypsin binding activity (greater than 96%) and by the characteristic increase in electrophoretic mobility, when analyzed by nondenaturing PAGE. Monomeric $\alpha_2$M was prepared by exposing the native form of the protein to a high concentration of DTT (2 mM) under non-denaturing conditions, as described by Moncino et al. *Biochem. Biophys. Res. Comm.* 200, 1578–1585 (1994). Incompletely dissociated $\alpha_2$M was separated from the monomers by FPLC on Superose-6. Monomeric $\alpha_2$M, which is prepared as described, does not re-associate at 22° C.

Preparation of Constructs Encoding GST-$\alpha_2$M-Peptide Fusion Proteins

The human $\alpha_2$M cDNA in pAT 153/PvuII/8 (pAT-$\alpha_2$M) was obtained from the ATCC (*Proc. Natl. Acad. Sci. U.S.A.* 82, 2282–2286 (1985)). Restriction digest analysis revealed an additional SacI cleavage site, which was not predicted by the published sequence, due to a single base substitution at nucleotide 2431 (C→T). To generate a construct encoding GST-$\alpha_2$M peptide-fusion protein-1 (FP1), a fragment from pAT-$\alpha_2$M that encodes amino acids 122–415 was excised with BstXI, blunt-ended with T4 DNA polymerase, and ligated into pGEX-3X at the SmaI site. The construct encoding FP2 was prepared by digesting pAT-$\alpha_2$M with EcoRI and NsiI, to yield a partial cDNA encoding amino acids 364–712, which was further digested with SacdI, to generate a cDNA encoding amino acids 364–613. This fragment was blunt-ended and ligated into pGEX-2T at the SmaI site. Constructs encoding FP3 and FP4 were prepared by isolating cDNAs, from a SacI digest of pAT-$\alpha_2$M, corresponding to amino acids 614–797 and 798–1082, respectively. These cDNAs were blunt-ended and ligated into the SmaI site of pGEX-2T. The construct encoding FP5 was prepared by digesting pAT-$\alpha_2$M with XhoI and PstI. A resulting cDNA, which encodes amino acids 1053–1302, was blunt-ended and ligated into pGEX-2T at the SmaI site. Restriction digest analysis of the five constructs confirmed that the $\alpha_2$M cDNA inserts were in the correct orientation. FIG. 1 shows the relationship of the five peptides to the intact structure of $\alpha_2$M.

Purification of GST-$\alpha_2$M-Peptide Fusion Proteins

BL21 cells harboring pGEX-$\alpha_2$M-peptide expression constructs were induced with 0.1 mM IPTG for 3 h at 37° C., harvested by centrifugation, and resuspended in 50 mM Tris-HCl, 100 mM NaCl, 10 mM EDTA, 1 mM EGTA, pH 8.0. Nearly-pure fusion protein preparations were generated by treating bacterial suspensions with 1 mg/ml lysozyme for 15 min on ice. The suspensions were then sonicated and subjected to centrifugation at 12,000×g for 10 min. All five fusion proteins remained in the insoluble fraction. These fractions were suspended in 10 mM deoxycholate for 2 h, sonicated, and subjected to a second centrifugation step. The fusion proteins, which again remained in the insoluble fractions, were solubilized by sonication in 2.0% SDS. To block free sulfhydryls, each fusion protein was reacted with 1 mM IAM in SDS for 2 h at 25° C. The IAM was then removed by dialysis. Final fusion protein preparations were stored in SDS. Protein concentrations were determined by the bicinchoninic acid (BCA) method.

Highly purified preparations of FP3 and FP4 were isolated in the absence of SDS by treating the original lysozyme extracts with 1.5% (w/v) Sarkosyl and 5 mM DTT. The FP3 and FP4, which solubilized in the Sarkosyl, were passed sequentially through 18 and 25-gauge needles and subjected to centrifugation at 12,000×g. The supernatants, which contained the fusion proteins, were treated with Triton X-100 (2% v/v) to sequester the Sarkosyl and then subjected to affinity chromatography on glutathione-Sepharose 4B. FP3 and FP4, which eluted from the column, were dialyzed against Sarkosyl (1.5%)/DTT (1 mM) and treated with IAM (5 mM) for 2 h at 25° C. to block free sulfhydryl groups. The final preparations were then dialyzed extensively against PBS.

Ligand Blotting

Native $\alpha_2$M, $\alpha_2$M-MA, MUG, and BSA were incubated in 2% SDS, in the presence or absence of 1 mM DTT, for 30 min at 37° C. To block free sulfhydryls, some samples were treated with 5 mM IAM for 2 h at 25° C. Equivalent amounts of each protein (5 Vtg) were subjected to SDS-PAGE on 10% slabs. IAM-treated GST-$\alpha_2$M-peptide fusion proteins were subjected to SDS-PAGE as well. All samples were electro-transferred to PVDF membranes. The membranes were blocked with 5% milk and 0.1% Tween 20 in PBS for 12 h at 4° C. and then rinsed with 0.1% Tween 20 in PBS (PBS-T). Membranes with native $\alpha_2$M, $\alpha_2$M-MA, MUG, and BSA were probed with $^{125}$I-TGF-$\beta$2 (20 pM), $^{125}$I-TGF-$\beta$1 (20 pM) or $^{125}$I-NGF-$\beta$ (50 pM) for 2 h at 25° C.; membranes with the five GST-$\alpha_2$M-peptide fusion proteins were probed with $^{125}$I-TGF-$\beta$2. The TGF-$\beta$1 and TGF-$\beta$2 were radioiodinated, to a specific activity of 100–200 µCi/µg, as previously described (*Biochem. Biophys. Res. Commun.* 138, 714–719 (1986)). NGF-$\beta$ was radioiodinated with Iodogen, to a specific activity of 2–5 µCi/µg, using the method recommended by the manufacturer. To determine whether TGF-$\beta$-binding to FP3 is noncovalent and specific, membranes containing immobilized FP3 (0.5 µg) were incubated with $^{125}$I-TGF-$\beta$1 (0.25 nM) or $^{125}$I-TGF-$\beta$2 (0.25 nM) in the presence of unlabeled TGF-$\beta$1 (200 nM), unlabeled TGF-$\beta$2 (200 nM), or solution-phase FP3 (1.0 µM). After washing the membranes with PBS-T, bound radioligands were detected by PhosphorImager analysis.

Western Blot Analysis

GST-$\alpha_2$M-peptides fusion proteins were subjected to SDS-PAGE and electro-transferred to nitrocellulose membranes. The membranes were blocked with 5% milk in PBS-T for 12 h at 4° C., incubated with a polyclonal antibody that recognizes GST, and then with peroxidase-conjugated goat-anti-rabbit IgG. Binding of secondary antibody was detected by enhanced chemiluminescence (Amersham).

Binding of $^{125}$I-TGF-$\beta$2 to FP3 and FP4 as Determined by FPLC $^{125}$I-TGF-$\beta$2 (0.5 nM) was incubated with FP3 or FP4 (0.5 µM) in PBS for 30 min at 37° C. The FP3 and FP4 were purified by glutathione-affinity chromatography, treated with IAM, and free of detergents. $^{125}$I-TGF-$\beta$2-fusion protein complexes were separated from free $^{125}$I-TGF-$\beta$2 by FPLC on prepacked Superose-12 columns. The flow rate was 0.4 ml/min. Elution of FP3 or FP4 was detected by monitoring the absorbance at 280 nm. $^{125}$I-TGF-$\beta$2 was detected in elution fractions using a gamma counter. To calibrate the FPLC, the following proteins were subjected to chromatography on the same column: soybean trypsin inhibitor ($M_r$~21,500, $V_e$ of 14.1 ml), ovalbumin ($M_r$~45,000, $V_e$ of 12.9 ml), BSA ($M_r$~66,000, $V_e$ of 12.1 ml), and BSA dimer ($M_r$~132,000, $V_e$ of 10.9 ml).

$^{125}$I-TGF-$\beta$ Binding to Immobilized $\alpha_2$M-MA $\alpha_2$M-MA (1 µg in 100 µl) was incubated in 96-well microtiter plates for 4 h at 22° C., as previously described (33). This procedure results in the immobilization of approximately 90 fmol of $\alpha_2$M-MA. The wells were washed three times with PBS-T and blocked with PBS-T for 16 h at 4° C. As a control, some wells were blocked with PBT-T without first immobilizing $\alpha_2$M-MA. $^{125}$I-TGF-$\beta$1 or $^{125}$I-TGF-$\beta$2 (0.1 nM) were incubated with the immobilized $\alpha_2$M-MA in the presence of increasing concentrations of FP3 or FP4 (4–250 nM) for 1 h at 22° C. The fusion proteins were purified and detergent-free. The wells were then washed three times with PBS-T. $^{125}$I-TGF-$\beta$, which was associated with the immobilized phase, was recovered in 0.1 M NaOH, 2% SDS and quantitated in a gamma counter. Results were analyzed by plotting the specific binding of $^{125}$I-TGF-$\beta$ versus the log of the fusion protein concentration. In these experiments, the concentration of TGF-$\beta$ (1 or 2) was at least 100-fold lower than the $K_D$ for TGF-$\beta$-binding to immobilized $\alpha_2$M-MA. Thus, TGF-$\beta$-binding was linearly related to the free TGF-$\beta$ concentration ($\beta_F$), according to the following equation: $B=(B_{max}/K_D)[\beta_F]$. In the presence of a fusion protein (FP) which binds TGF-$\beta$, the total concentration of TGF-$\beta$ [$\beta_T$] was related to [$\beta_F$], at equilibrium, as follows: $[\beta_T]=[\beta_F](1+[FP]/K_I)$. If the fusion protein-TGF-$\beta$-complex did not bind to immobilized $\alpha_2$M-MA, then TGF-$\beta$-binding was reduced by 50% (the IC$_{50}$) when $[\beta_T]/[\beta_F]=2$ and the fusion protein concentration which yielded the IC$_{50}$ was equal to the $K_I$.

Endothelial Cell Proliferation Assays

Fetal bovine heart endothelial (FBHE) cells were cultured in DMEM supplemented with 10% FBS, 20 ng/ml acidic fibroblast growth factor, and 80 ng/ml basic fibroblast growth factor and passaged at subconfluence with trypsin-EDTA. To perform proliferation assays, the cells were plated at a density of $2\times10^4$/well (24 well plates) in DMEM supplemented with 0.2% FBS. The cells were pulse-exposed to TGF-$\beta$1 or TGF-$\beta$2 (10 pM), in the presence and absence of FP3 or FP4 (200 nM), for 1 h. The fusion proteins were preincubated with the TGF-$\beta$ for 15 min prior to addition to the cultures. At the completion of an incubation, the cultures were washed 3 times with serum-free DMEM and then allowed to incubate in DMEM with 0.2% FBS for 30 h. [$^3$H]Thymidine was added for an additional 18 h; the cells were then harvested and [$^3$H]thymidine incorporation was quantitated.

Nitric Oxide Synthesis

NO synthesis by RAW 264.7 cells was quantitated by measuring the stable NO oxidation product, nitrite, in conditioned medium, as previously described (*Anal. Biochem.* 126, 131–138 (1982)). Cells were plated at a density of $10^4$/well in 96-well plates and cultured in RPMI 1640 with 10% FBS for 24 h and then in RPMI 1640 without serum (SFM) for an additional 24 h. $\alpha_2$M-MA, FP3, FP4, or GST were added separately to the cultures, in SFM. The fusion proteins were purified and detergent-free. After 24 h, conditioned medium (100 $\mu$l) was recovered and nitrite was measured. It has been previously reported that $\alpha_2$M increases RAW 264.7 cell NO synthesis by neutralizing endogenously-produced TGF-$\beta$ (*J. Biol, Chem.* 270, 21919–21927 (1995)). The $\alpha_2$M-induced increase in RAW 264.7 cell NO synthesis is inhibited by the NOS inhibitor, N$^G$-monomethyl-L-arginine.

Results

Ligand Blot Analysis of $^{125}$I-TGF-$\beta$-binding to $\alpha_2$M

Native $\alpha_2$M, $\alpha_2$M-MA, and BSA were denatured in SDS (+/− reductant), subjected to SDS-PAGE, and electro-transferred to PVDF membranes. Some samples were treated with IAM prior to electrophoresis. The membranes were stained with Coomassie Blue, demonstrating nearly equivalent electro-transfer of the three proteins (results not shown). Unreduced $\alpha_2$M migrated as a single band with an apparent mass of 360-kDa, as expected; reduced $\alpha_2$M migrated as a single major band with an apparent mass of 180-kDa. Methylamine treatment did not alter the mobility of $\alpha_2$M.

Figure 2:
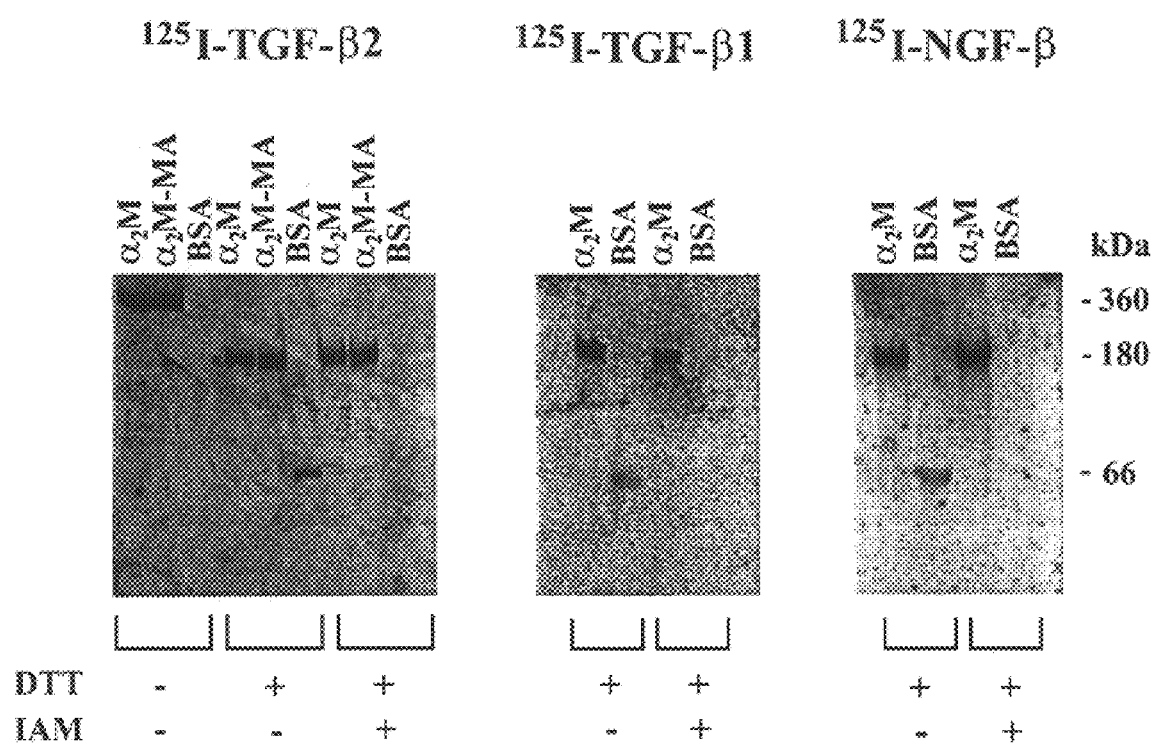
FIG. 2. Ligand blot analysis of $^{125}$I-cytokine binding to native $\alpha_2$M, $\alpha_2$M-MA and BSA. Native $\alpha_2$M, $\alpha_2$M-MA, and BSA were denatured in 2% SDS, with or without 1 mM DTT, for 30 min at 37° C. Some samples were subsequently treated with 5 mM IAM for 2 h at 25° C. DTT or IAM-treated samples are marked "+" in the respective rows. All samples were subjected to SDS-PAGE and electro-transferred to PVDF membranes. The membranes were blocked and incubated with the indicated cytokines for 2 h at 25° C. Cytokine-binding was detected by PhosphorImager analysis.

$^{125}$I-TGF-$\beta$2 bound to native $\alpha_2$M and $\alpha_2$M-MA, which were immobilized on PVDF membranes (FIG. 2). $^{125}$I-TGF-$\beta$2-binding was unchanged when the $\alpha_2$M was treated with DTT or with IAM, prior to electrophoresis. $^{125}$I-TGF-$\beta$2 also bound to BSA; however, this interaction was observed only after DTT-treatment and was eliminated by treating the BSA with IAM. Thus, binding of $^{125}$I-TGF-$\beta$2 to reduced BSA probably involves free sulfhydryl groups that are not available in the native BSA structure. The ability of isolated $\alpha_2$M subunits to bind $^{125}$I-TGF-$\beta$2, by an IAM-insensitive mechanism, suggests that the ligand blotting system accurately models the interaction of TGF-$\beta$ with non-denatured $\alpha_2$M and that $\alpha_2$M quaternary structure is not necessary for this interaction.

To further assess the growth factor-binding activity of isolated $\alpha_2$M subunits, in the ligand blotting system, studies were performed with $^{125}$I-TGF-$\beta$1 and $^{125}$I-NGF-$\beta$. These two cytokines bind to non-denatured $\alpha_2$M with similar affinity. As shown in FIG. 2, $^{125}$I-TGF-$\beta$1 and $^{125}$I-NGF-$\beta$ both bound to immobilized $\alpha_2$M by an IAM-insensitive mechanism. Reductant-treated BSA also bound $^{125}$I-TGF-$\beta$1 and $^{125}$I-NGF-$\beta$; however, this interaction was eliminated when the BSA was treated with IAM.

Ligand Blot Analysis of the Binding of $^{125}$I-TGF-$\beta$2 to MUG

Figure 3:
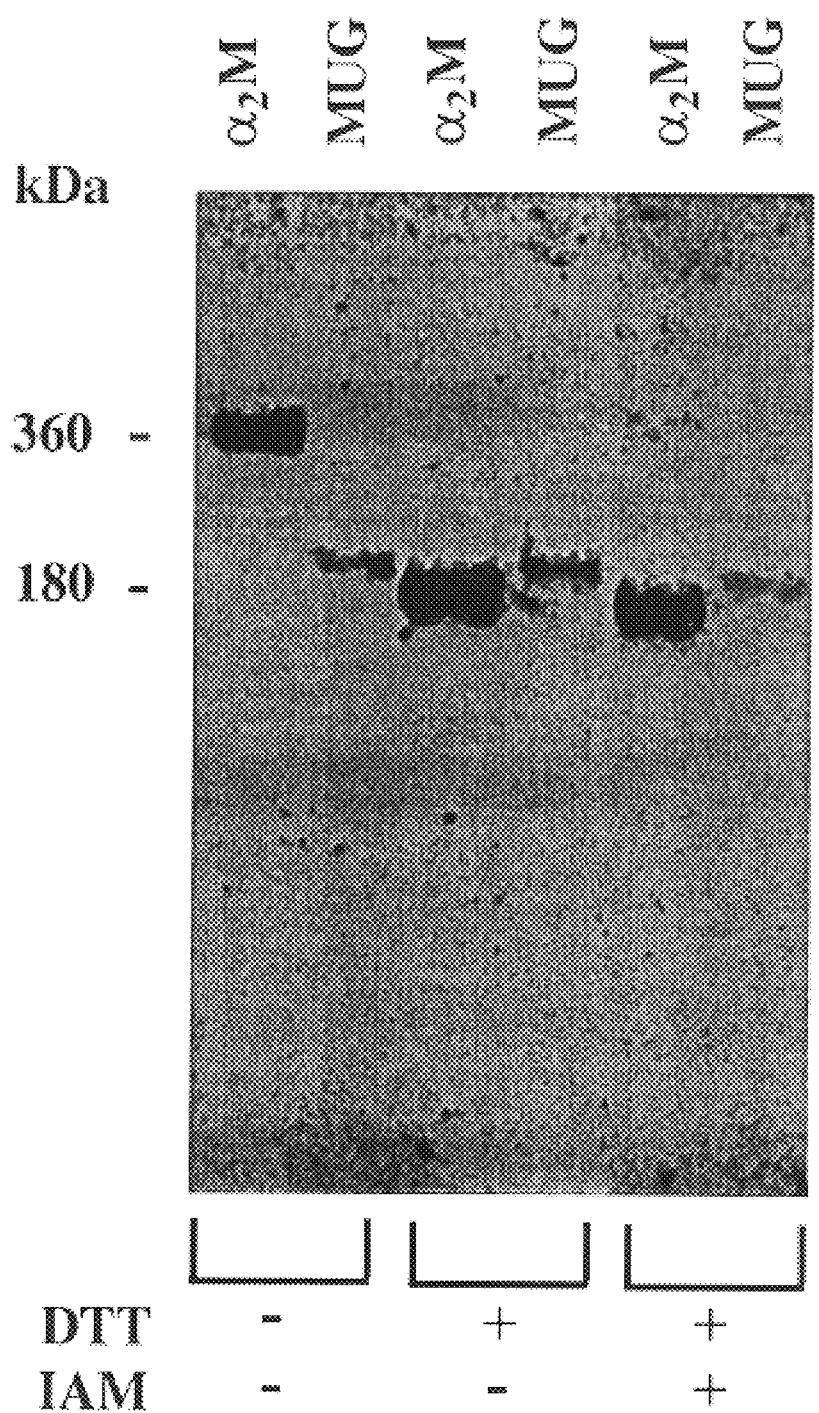
FIG. 3. $^{125}$I-TGF-β2 binding to $\alpha_2$M and MUG, as determined by ligand blot analysis. Native $\alpha_2$M and MUG were denatured in SDS. Samples that were DTT- or IAM-treated are designated by "+" signs. All samples were subjected to SDS-PAGE and electro-transferred to PVDF membranes. The membranes were blocked and incubated with $^{125}$I-TGF-β2 for 2 h at 25° C. $^{125}$I-TGF-β2-binding was detected by PhosphorImager analysis.

MUG is a monomeric murine homologue of human $\alpha_2$M. Although tetrameric murine $\alpha_2$M, in its native form, binds TGF-$\beta$1 and TGF-$\beta$2 comparably to human $\alpha_2$M, MUG does not bind either TGF-$\beta$ isoform with significant affinity ($K_D$~1.0 $\mu$M). Thus, we compared the binding of $^{125}$I-TGF-$\beta$2 to human $\alpha_2$M and MUG, as another test of the validity of the ligand-blotting method. As shown in FIG. 3, only trace levels of $^{125}$I-TGF-$\beta$2 bound to MUG and the amount of binding was decreased when the MUG was treated with IAM. These results support the hypothesis that ligand-blotting is a valid method for the analysis of cytokine-binding to $\alpha$-macroglobulins. Apparently, MUG does not contain a cryptic TGF-$\beta$-binding site that is exposed by SDS-treatment.

TGF-$\beta$2-Binding to GST-$\alpha_2$M-Peptide Fusion Proteins

Figure 4:
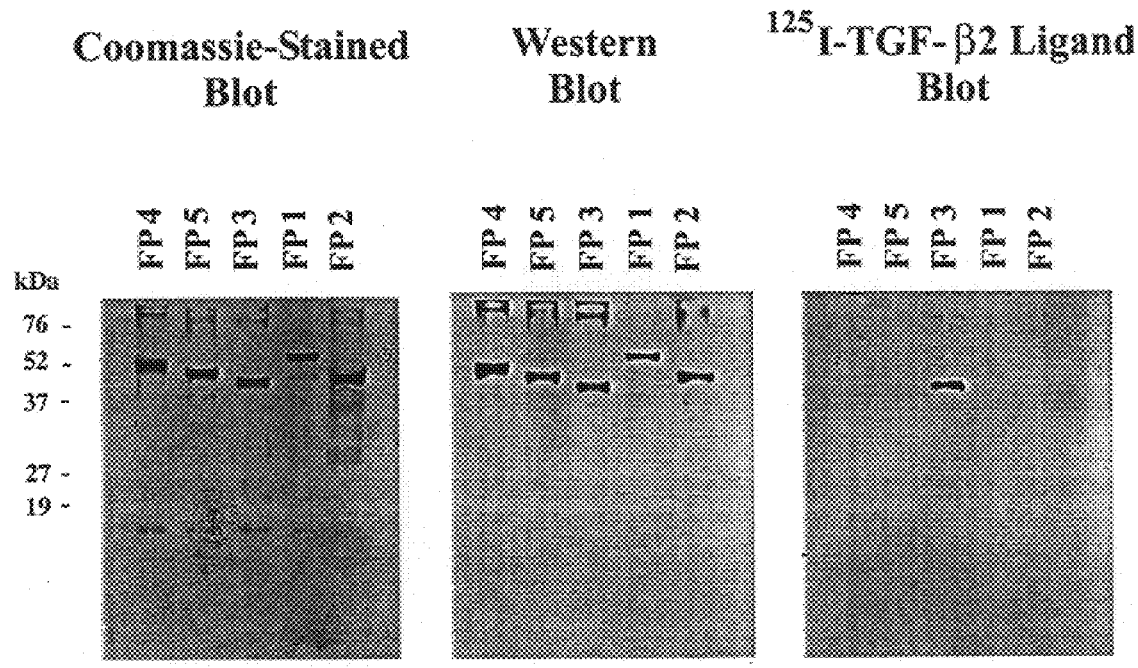
FIG. 4. Binding of $^{125}$I-TGF-β2 to GST-$\alpha_2$M-peptide-fusion proteins. The five fusion proteins (FP1–FP5) were subjected to SDS-PAGE and electro-transferred to PVDF or nitrocellulose membranes. PVDF membranes were stained with Coomassie Blue. Western blot analysis was performed with an anti-GST IgG fraction of antiserum. Ligand blot analysis was performed with $^{125}$I-TGF-β2. After incubation for 2 h, $^{125}$I-TGF-β2-binding was detected by Phosphorimager analysis.

The five fusion proteins were subjected to SDS-PAGE and electro-transferred to PVDF. The electrophoretic mobility of the major Coomassie-stained band, in each preparation, indicated a molecular mass which was identical to the mass of the monomeric fusion protein predicted by the cDNA sequence (FIG. 4). Western blot analysis with a GST-specific antibody confirmed that the major band in each lane was a GST-fusion protein. The low-mobility bands also bound GST-specific antibody and thus most likely represent SDS-insensitive fusion protein aggregates. In ligand blotting experiments, FP3 bound $^{125}$I-TGF-$\beta$2. Since all five fusion proteins were IAM-treated, free sulfhydryl groups in FP3 did not account for the $^{125}$I-TGF-$\beta$2-binding. FP1, FP2, FP4, FP5, and purified GST (not shown) did not bind $^{125}$I-TGF-$\beta$2.

In separate ligand blotting experiments, affinity-purified FP3 bound TGF-$\beta$2 comparably to the FP3 which was stored in SDS (results not shown). Thus, the two preparations were interchangeable when analyzed by this method. In order to demonstrate that $^{125}$I-TGF-$\beta$-binding to FP3 is noncovalent and specific, $^{125}$I-TGF-$\beta$ was incubated with PVDF-immobilized FP3 in the presence of excess solution-phase FP3 or unlabeled TGF-$\beta$. FP3 (1 $\mu$M) in solution inhibited the binding $^{125}$I-TGF-$\beta$1 and $^{125}$I-TGF-$\beta$2 to immobilized FP3 by 94±3% and 92±5%, respectively. Unlabeled TGF-$\beta$1 (0.2 $\mu$M) inhibited $^{125}$I-TGF-$\beta$1 binding to immobilized FP3 by 72±8%; unlabeled TGF-β2 (0.2 μM) inhibited $^{125}$I-TGF-β2 binding to immobilized to FP3 by 90±4%.

Figure 5A:
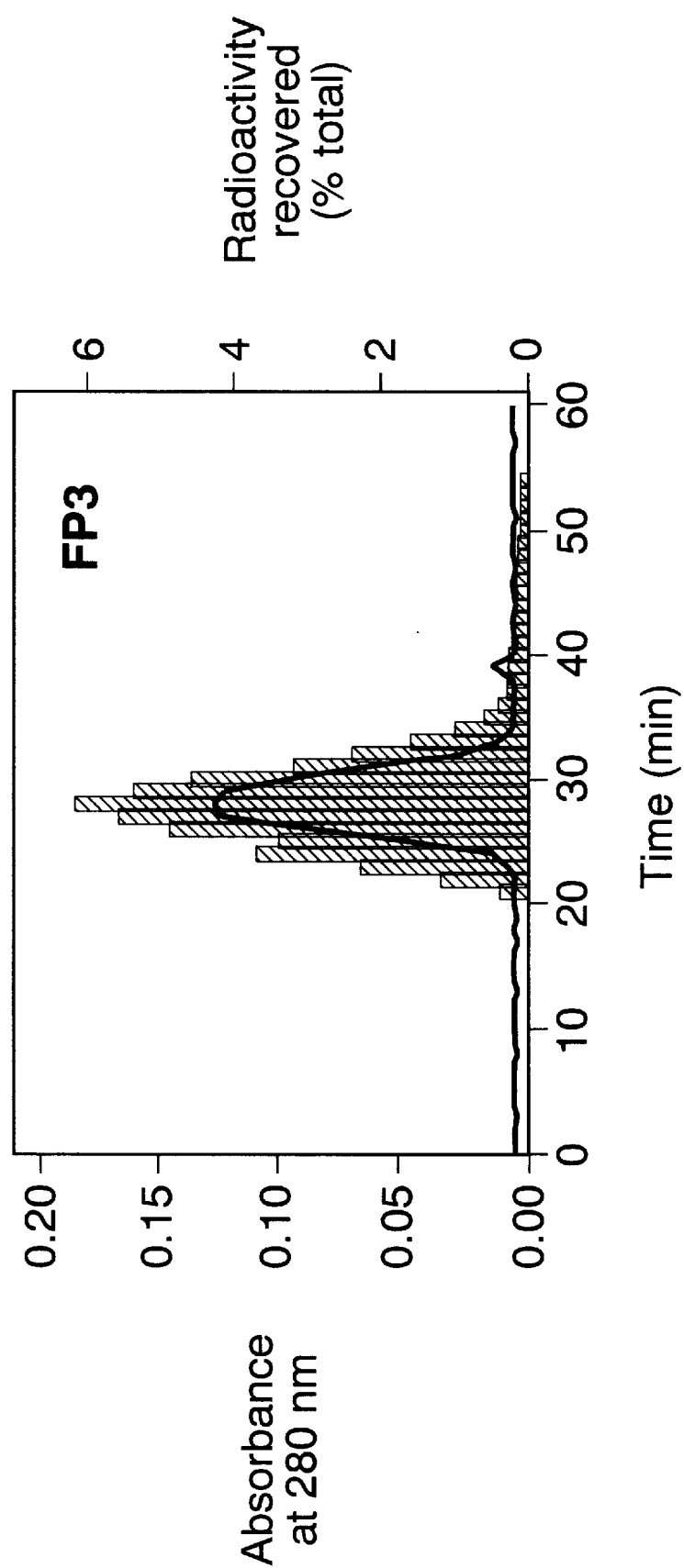
FIG. 5. Binding of $^{125}$I-TGF-β2 to purified FP3 as determined by FPLC. FP3 and FP4 were incubated with $^{125}$I-TGF-β2 for 30 min at 37° C. and then subjected to FPLC on a Superose-12 column. Radioactivity recovery in each fraction is plotted as a percent of the originally loaded radioactivity. The solid tracings show the absorbance of the eluate at 280 nm as a function of time.
Figure 5B:
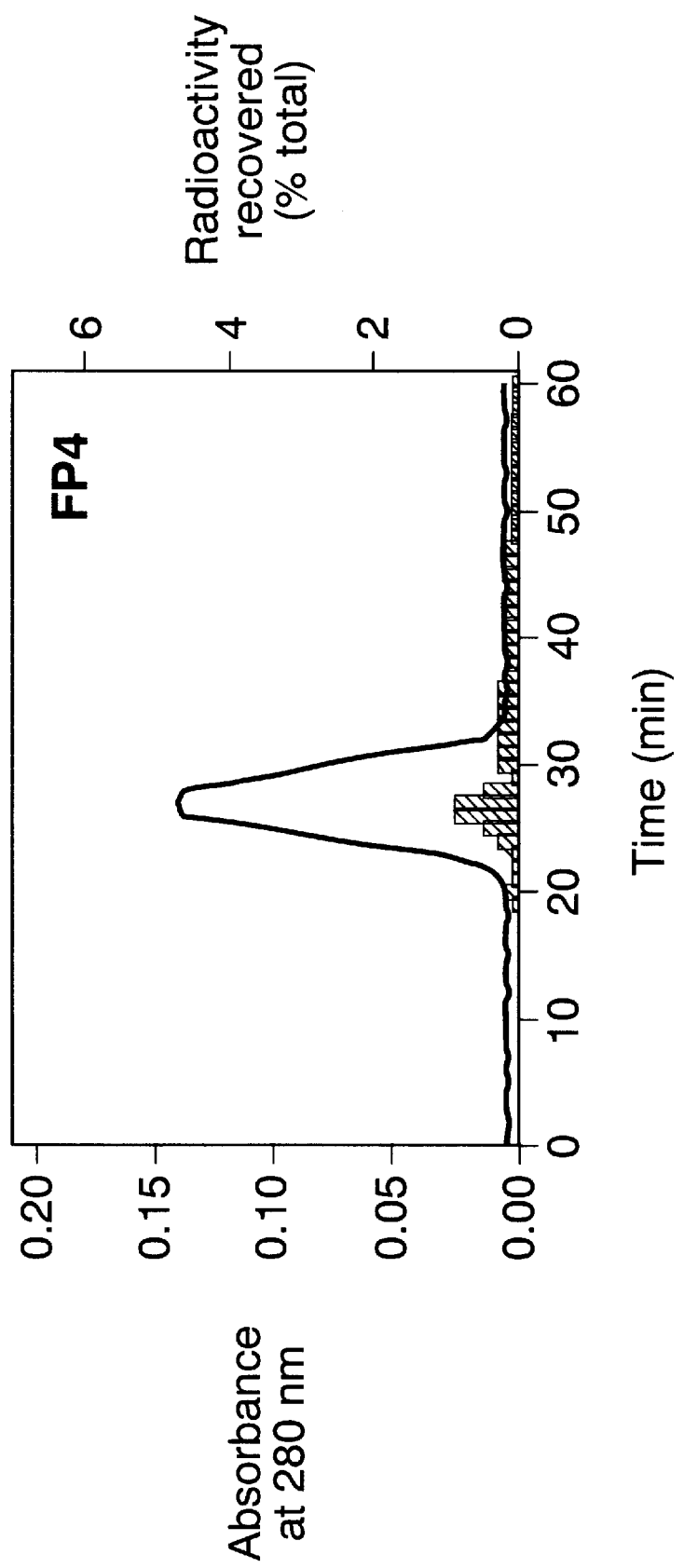

Binding of $^{125}$I-TGF-β2 to FP3 in Solution $^{125}$I-TGF-β2 (0.5 nM) was incubated with FP3 or FP4 (0.5 μM) in solution, in the absence of detergents. Free and fusion protein-associated $^{125}$I-TGF-β2 were separated by FPLC on Superose-12. It has been previously reported that free TGF-β interacts substantially with Superose and thus is recovered slowly at volumes that exceed the totally-included volume (J. Clin. Invest. 87, 39–44 (1991)). As shown by the absorbance tracings (280 nm) in FIG. 5, FP3 and FP4 eluted at volumes suggesting that these fusion proteins are dimers. The $V_e$s were 11.4 and 11.2 ml for FP3 and FP4, respectively, corresponding to apparent masses of 95- and 107-kDa. Other GST-fusion proteins are also expressed as noncovalent dimers. Substantial amounts of radioactivity co-eluted with FP3; 42% of the $^{125}$I-TGF-β2 was recovered with this fusion protein (n=2). By contrast, only 6% of the TGF-β2 co-eluted with FP4. FPLC is a non-equilibrium method for assessing protein-protein interactions. The amount of complex detected may be significantly lower than that which was initially present.

$^{125}$I-TGF-β-Binding to Immobilized α$_2$M-MA $^{125}$I-TGF-β1 and $^{125}$I-TGF-β2 (0.1 nM) were incubated in separate α$_2$M-MA-coated microtiter wells for 1 h; 3.4±0.3 fmol of $^{125}$I-TGF-β1 and 2.6±0.2 fmol of $^{125}$I-TGF-β2 bound to the immobilized α$_2$M-MA. Unlabeled TGF-β (0.2 μM) decreased the binding of $^{125}$I-TGF-β by greater than 75%. $^{125}$I-TGF-β recovery in the immobilized phase was decreased by greater than 95% when the wells were not pre-coated with α$_2$M-MA.

Figure 6A:
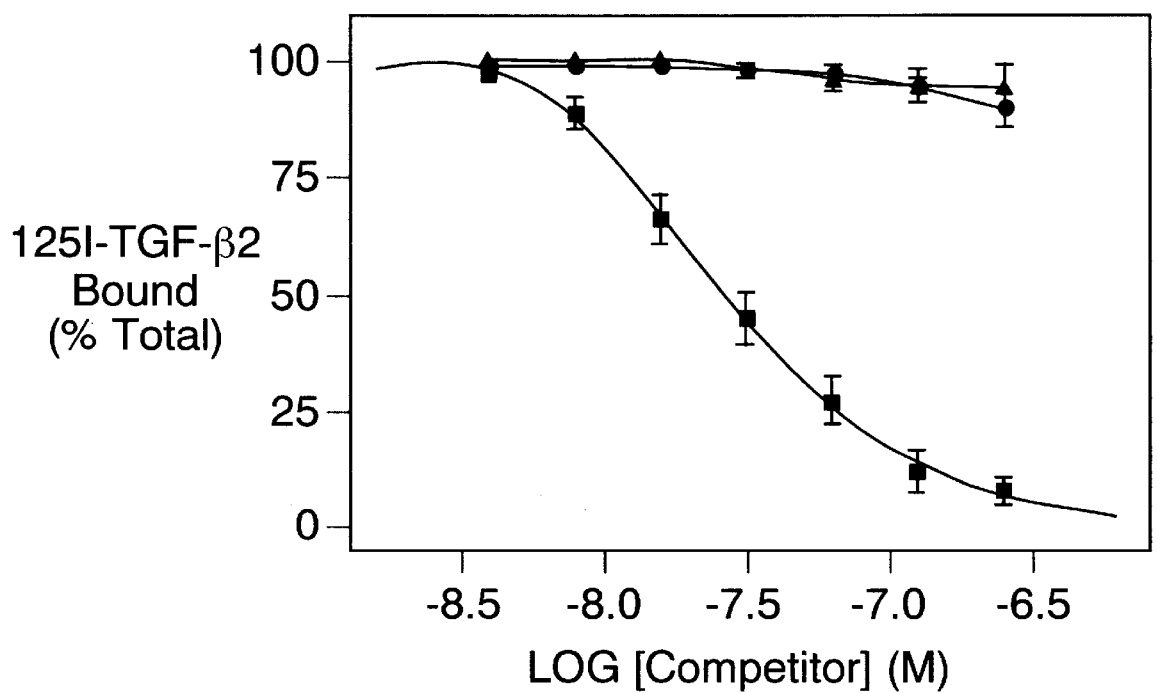
FIG. 6. Binding of $^{125}$I-TGF-β to immobilized $\alpha_2$M-MA in the presence of FP3 and FP4. In panel A, $^{125}$I-TGF-β2 was incubated in $\alpha_2$M-MA-coated wells in the presence of increasing concentrations of affinity-purified FP3 (■), FP4 (●), or GST (▲) (the concentration of fusion protein was based on the molecular mass of the monomer). In panel B, $^{125}$I-TGF-β1 was incubated in $\alpha_2$M-MA-coated wells in the presence of increasing concentrations of affinity-purified FP3 (■) or GST (▲). Incubations were conducted for 1 h at 22° C. After washing, $^{125}$I-TGF-β, which was bound to the immobilized phase, was recovered in 0.1 M NaOH, 2% SDS. Radioactivity was quantitated in a gamma counter (mean±S.E., n=4).
Figure 6B:
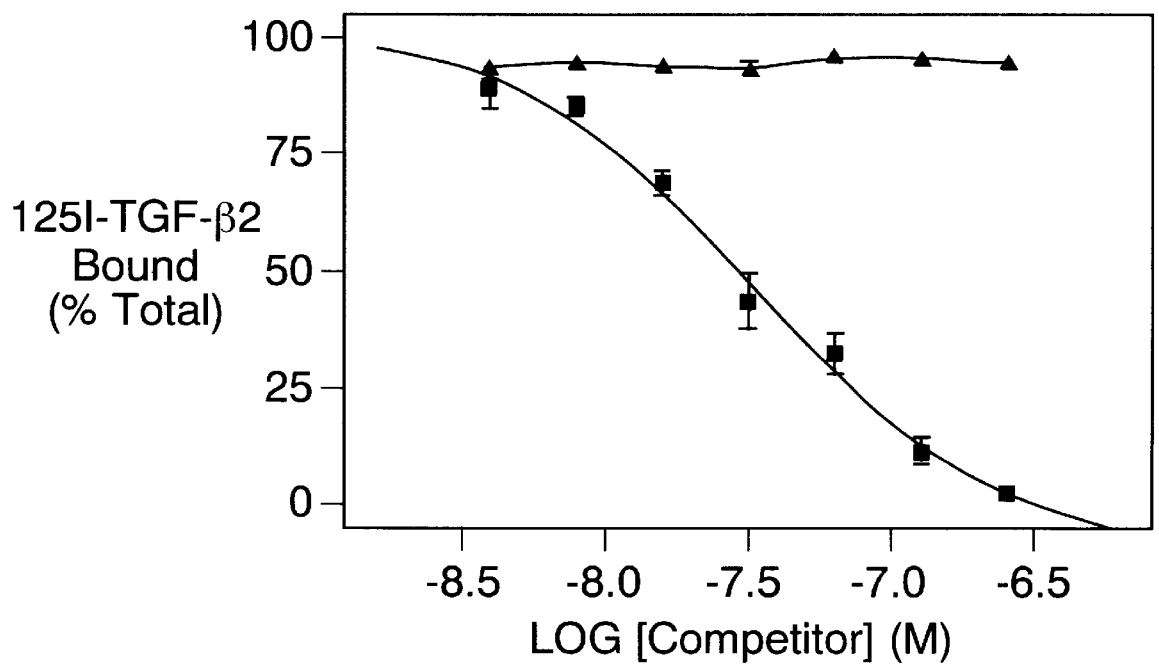

Various concentrations of FP3, FP4 or GST were added, with $^{125}$I-TGF-β1 or $^{125}$I-TGF-β2, to α$_2$M-MA-coated microtiter wells. FP3 inhibited the binding of $^{125}$I-TGF-β1 and $^{125}$I-TGF-β2 to immobilized α$_2$M-MA, in a concentration-dependent manner (FIG. 6). Nearly complete inhibition was observed when the concentration of FP3 exceeded 100 nM; this result indicates that TGF-β-FP3 complex does not bind to α$_2$M-MA. The IC$_{50}$ was 33±5 nM in experiments with TGF-β1 and 26±6 nM in experiments with TGF-β2. If binding of a single FP3 to TGF-β eliminates the ability of the TGF-β to bind to α$_2$M-MA, then the IC$_{50}$ provides an accurate estimate of the K$_D$; if more than one FP3 must bind, then the K$_D$ is lower than the IC$_{50}$. FP4 and GST did not inhibit the binding of $^{125}$I-TGF-β2 to immobilized α$_2$M-MA. GST also failed to inhibit the binding of $^{125}$I-TGF-β1 to immobilized α$_2$M-MA.

Table I summarizes studies comparing the activities of FP3, native α$_2$M, monomeric α$_2$M, α$_2$M-MA, and thrombospondin, as solution-phase inhibitors of the binding of TGF-β to immobilized α$_2$M-MA. The IC$_{50}$ values determined for FP3, native α$_2$M, and α$_2$M-MA, in studies with TGF-β2, were all similar even though the effective sequence in FP3 is contained in quadruplicate within the structure of intact, homotetrameric α$_2$M. The IC$_{50}$ determined for TGF-β1 and FP3 was slightly lower than that determined with α$_2$M-MA and substantially lower than that determined with native α$_2$M. Interestingly, monomeric α$_2$M bound TGF-β1 with slightly increased affinity compared with native α$_2$M, even though each mol of native α$_2$M contains four mol of monomer. This result may be explained if the affinity of TGF-β1 for its binding site in tetrameric α$_2$M is decreased compared with the affinity for the same site in monomeric α$_2$M and/or the number of available TGF-β-binding sites within tetrameric α$_2$M is less than four.

TABLE I

Concentration of unlabeled competitor that decreases $^{125}$I-TGF-β binding to immobilized α$_2$M-MA by 50% (IC$_{50}$ values)
The IC$_{50}$ values for α$_2$M, α$_2$M-MA, and thrombospondin were previously reported in references 31 and 33. All values represent the mean ± S.E.; n = 4

| Competitor | TGF-β1 | TGF-β2 |
| --- | --- | --- |
| FP3 | 33 ± 5 nM | 26 ± 6 nM |
| α$_2$M | 520 ± 39 nM | 19 ± 3 nM |
| α$_2$M-MA | 79 ± 9 nM | 19 ± 5 nM |
| α$_2$M monomer | 360 ± 48 nM | — |
| Thrombospondin | 160 ± 18 nM | — |

FBHE Proliferation Assays

To determine whether FP3-binding inhibits TGF-β activity, FBHE proliferation assays were performed. The cells were pulse-exposed to TGF-β1 or TGF-β2 (10 pM) for 1 h, in the presence and absence of FP3 or FP4. [$^3$H] Thymidine incorporation was measured 30 h later. As shown in Table II, [$^3$H]thymidine incorporation was decreased 69% and 57% by TGF-β1 and TGF-β2, respectively. No change in TGF-β activity was observed when FP4 was included in the medium. By contrast, FP3 nearly completely inhibited the activities of both TGF-β1 and TGF-β2, increasing [$^3$H] thymidine incorporation to within 3% and 6% of the control values.

TABLE II

Effects of Fusion Proteins on TGF-β activity in an endothelial cell proliferation assay FBHE cells were pulsed-exposed to TGF-β (10 pM), FP3 (0.2 μM), FP4 (0.2 μM), or fusion protein + TGF-β for 1 h. The fusion proteins were pre-incubated with TGF-β for 15 min at 37° C. before addition to the FBHE cultures. After 30 h, 1 μCi/ml [$^3$H]thymidine was added to the cultures for an additional 18 h. [$^3$H]Thymidine incorporation was determined as a percentage of that observed in control cultures which were not treated with TGF-β or fusion protein.

| Agent added | [$^3$H]thymidine incorporation (% control) |
| --- | --- |
| TGF-β1 | 31 ± 3 nM |
| TGF-β2 | 43 ± 2 nM |
| FP3 + TGF-β1 | 97 ± 5 nM |
| FP4 + TGF-β1 | 31 ± 4 nM |
| FP3 + TGF-β2 | 94 ± 6 nM |
| FP4 + TGF-β2 | 38 ± 6 nM |

Figure 7:
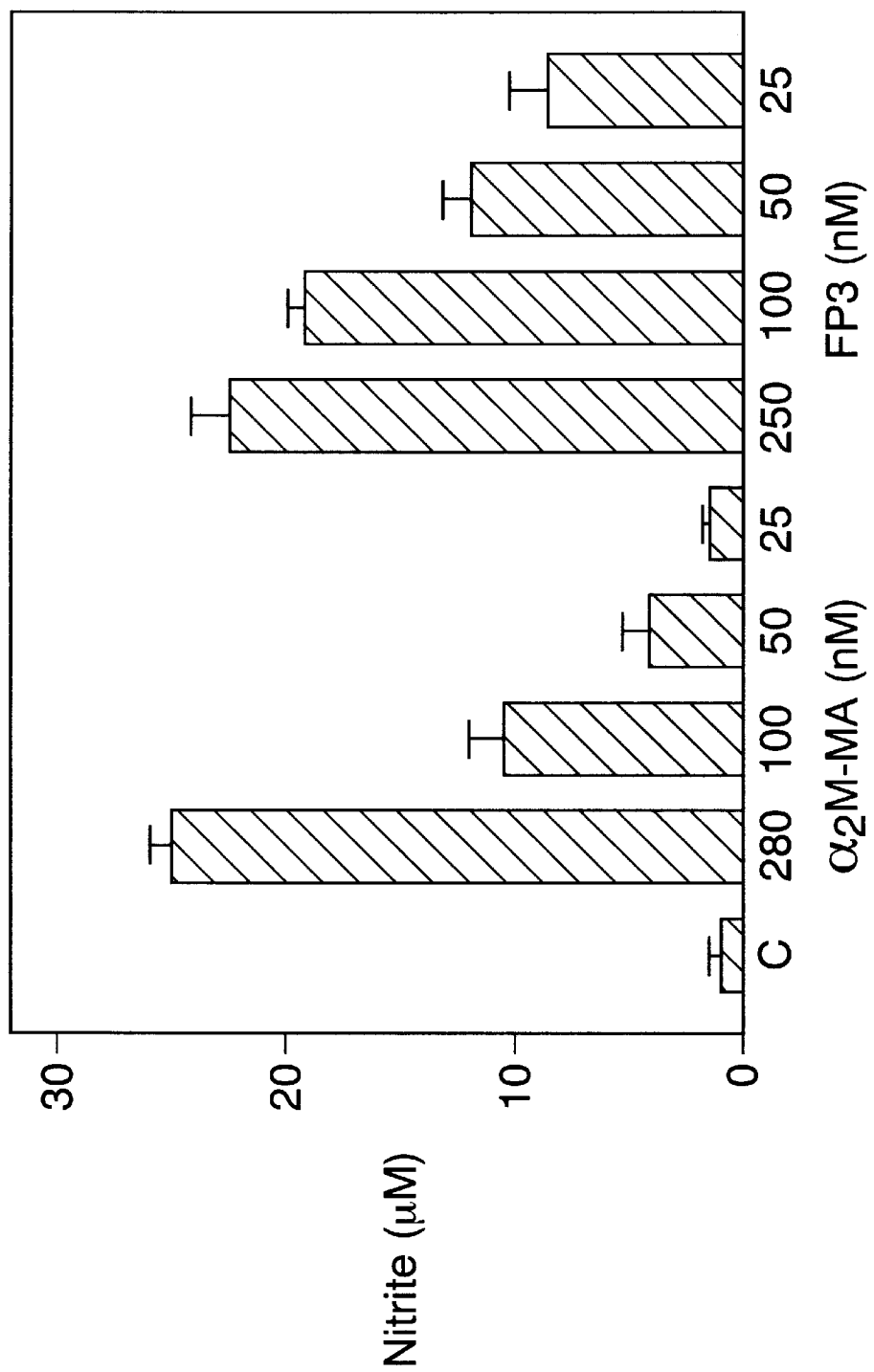
FIG. 7 NO synthesis by RAW 264.7 cells treated with FP3. RAW 264.7 cells were treated with $\alpha_2$M-MA or FP3 in SFM. The control (C) was incubated in SFM (no $\alpha_2$M-MA or FP3). After 24 h, nitrite levels in the conditioned media were measured. The presented results represent the mean±S.E. (n=4).
Figure 8:
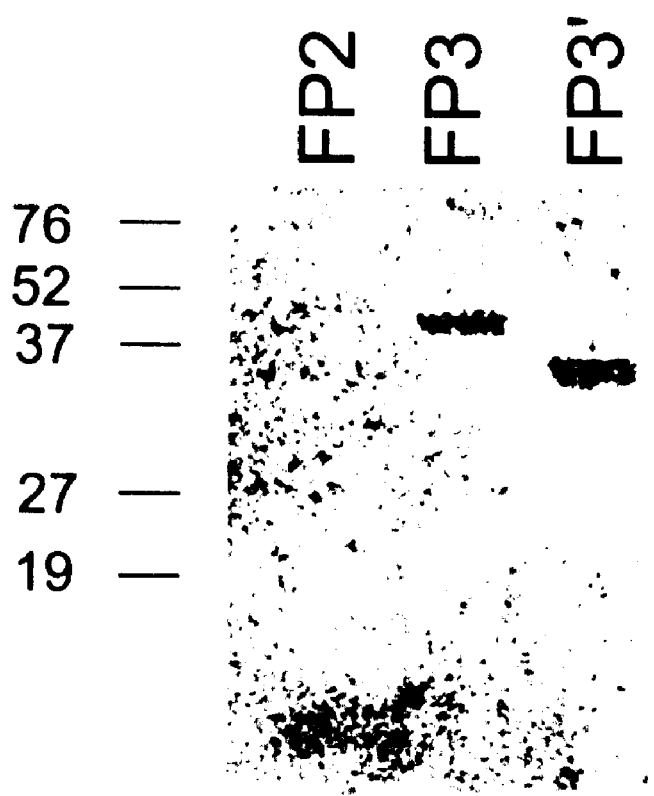
FIG. 8. Binding of $^{125}$I-TGF-β1 to GST-$\alpha_2$M-peptide-fusion proteins. Three fusion proteins (FP2, FP3 and FP3') were subjected to SDS-PAGE and electro-transferred to PVDF or nitrocellulose membranes. Ligand blot analysis was performed with $^{125}$I-TGF-β1.

Regulation of NO Synthesis by FP3 and FP4

α$_2$M neutralizes TGF-β, which is synthesized and activated endogenously by RAW 264.7 cells, and thereby induces expression of iNOS. In order to determine whether FP3 neutralizes the activity of endogenously-synthesized TGF-β, we assessed the ability of the fusion protein to induce the production of nitrite in RAW 264.7 cell-conditioned medium. As shown in FIG. 7, FP3 increased NO synthesis in a concentration-dependent manner and, at low concentrations, was more active than α$_2$M-MA. The increase in NO synthesis, which is induced by 280 nM α$_2$M-MA, is comparable to that observed with 10 ng/ml interferon-γ (J. Biol. Chem. 270, 21919–21927 (1995)). FP4 and purified GST (250 nM) did not increase nitrite production by the RAW 264.7 cells.

Discussion

When the majority of the α$_2$M cDNA was expressed in a series of five GST-fusion proteins, TGF-β-binding was localized exclusively to FP3. The other four fusion proteins and purified GST did not bind TGF-β. Selective binding of TGF-β to affinity-purified FP3, and not to FP4, was demonstrated by FPLC and by radioligand-binding competition assay. FP3 was more effective than native $\alpha_2$M or $\alpha_2$M-MA at inhibiting TGF-β-binding to immobilized $\alpha_2$M-MA, especially in experiments with TGF-β1. This result is intriguing for at least three reasons. Firstly, the concentrations of intact $\alpha_2$M tetramer and FP3 monomer were used for comparison, even though our FPLC results suggested that FP3 is a noncovalent dimer. If, instead, the $IC_{50}$ values are based on the concentration of the $\alpha_2$M "subunit", then the difference between FP3 and intact $\alpha_2$M is four-fold greater.

Secondly, the experimentally determined $IC_{50}$ values accurately estimate the $K_I$ only if one molecule of competitor is sufficient to completely prevent TGF-β-binding to immobilized $\alpha_2$M-MA; otherwise, the $K_I$ is lower than the $IC_{50}$. Although it is possible that two copies of FP3 or $\alpha_2$M are required to neutralize TGF-β, given the homodimeric structure of TGF-β, this possibility is considered less likely with intact $\alpha_2$M, due to its large size and complex structure. Also, tetrameric $\alpha_2$M may bind more than one molecule of TGF-β. Finally, FP3 may adopts a secondary and tertiary structure which is optimal for TGF-β-binding. Taken together, these results suggest that a specific sequence in FP3 binds TGF-β with relatively high affinity. The equivalent sequence may be partially masked within intact $\alpha_2$M, accounting for the observed decrease in TGF-β-binding affinity. The masking of the TGF-β-binding site in intact $\alpha_2$M may also explain why $\alpha_2$M conformational change markedly alters TGF-β-binding affinity.

Human $\alpha_2$M and bovine $\alpha_2$M bind TGF-β2 with increased affinity compared with TGF-β1, explaining why TGF-β1 is preferentially active in certain cell culture assays that require serum-supplemented medium. Danielpour and Sporn *J. Biol. Chem.* 265, 6973–6977 (1990) provided evidence that the α-macroglobulins from rabbit also preferentially bind TGF-β2. By contrast, murine $\alpha_2$M binds TGF-β1 and TGF-β2 with equivalent affinity (*J. Biol. Chem.* 271, 24982–24988 (1996)). As shown in FIG. 6 TGF-β1 and TGF-β2 bind to FP3 with equivalent affinity. This result suggests that the isoform-specificity in TGF-β-binding to certain α-macroglobulins may be due to the ability of TGF-β2 to preferentially access the FP3-binding site in the intact α-macroglobulin. When the structural constraints of intact $\alpha_2$M are eliminated, as in FP3, isoform-specificity in TGF-β-binding is no longer observed. NMR and x-ray crystallography studies have demonstrated the presence of small differences in the overall shape and structure of TGF-β1 and TGF-β2 and these small differences may account for why the binding site for TGF-β2 is "less masked" in the structure of intact human $\alpha_2$M compared with the binding site for TGF-β1.

In addition to the TGF-β-binding site, FP3 also contains the $\alpha_2$M bait region. Models have been developed regarding the location of the bait region within the complex three-dimensional structure of $\alpha_2$M based on electron microscopy, x-ray crystal structure (which has been solved at 10 Å resolution), NMR and EPR spectroscopy studies, and fluorescence resonance energy transfer studied. The overall structure of $\alpha_2$M resembles a hollow cylinder with a two-compartment central cavity. In $\alpha_2$M-proteinase complexes, the proteinases occupy the central cavities. The bait regions are located within the central cavities, towards the center of the $\alpha_2$M structure, and within 11–17 Å of the Cys residues (Cys-949) which form the thiol ester bonds. If in fact, the bait region and the TGF-β-binding site are equivalent or over-lapping, then the TGF-β-binding site may be accessible only from within the $\alpha_2$M central cavity. TGF-β-specific antibodies fail to recognize $\alpha_2$M-associated TGF-β, supporting the hypothesis that TGF-β occupies the central cavity; however, it is not clear whether the $\alpha_2$M, which was studied in the antibody experiments, was in the native or conformationally-altered form. Thus, the location of the FP3-binding site for TGF-β, within intact $\alpha_2$M, remains unresolved.

The stoichiometry of cytokine binding to $\alpha_2$M has been estimated at 1:1 or 2:1. The present data suggest that the binding site contained within a single $\alpha_2$M sub-unit may be sufficient to bind TGF-β. Thus, an estimate of four cytokine-binding sites per $\alpha_2$M does not seem unreasonable. Limitations in the number of cytokine-binding sites in intact $\alpha_2$M may result from steric hindrance. If $\alpha_2$M-associated cytokines occupy the central cavity, then the number of cytokines that bind may be limited by the available cavity space. Of equal importance is the possibility that a high affinity complex between $\alpha_2$M and TGF-β requires that the cytokine engage two equivalent copies of FP3 on different subunits. $K_D$ values, determined by the $\alpha_2$M-MA immobilization method and by a $BS^3$-crosslinking method (*J. Biol. Chem.* 269,1533–1540(1994) and *Arch. Biochem. Biophys.* 292, 487–49 (1992)), assume a single cytokine-binding site per $\alpha_2$M tetrarner. If there are two independent binding sites, then the $K_D$ for each site would be increased by a factor of two.

As shown in FBHE proliferation assays, FP3 not only binds TGF-β1 and TGF-β2, but also neutralizes the activities of these cytokines. When added to RAW 264.7 cell cultures, FP3 promoted the accumulation of nitrite more effectively than $\alpha_2$M-MA. Since NO synthesis by $\alpha_2$M is due to the neutralization of TGF-β, the increased potency of FP3 may be due to its increased binding affinity for TGF-β. To test this hypothesis, we measured the secretion of TGF-β1 and TGF-β2 by RAW 264.7 cells using isoform-specific ELISAs. In medium which was conditioned for 24 h, the concentrations of active and total (active+latent) TGF-β1 were 2 and 10 pM, respectively. The concentrations of active and total TGF-β2 were 1 and 4 pM, respectively. The active TGF-β levels reported here are only slightly lower than those determined previously using an endothelial cell growth assay. More importantly, the ELISA studies confirm that RAW 264.7 cells express both TGF-β isoforms but higher levels of TGF-β1, supporting the hypothesis that the increased potency of FP3 reflects its increased capacity to neutralize TGF-β1.

In summary, the peptide fragment FP3, isolated from the structure of $\alpha_2$M, contains the binding site for TGF-β1 and TGF-β2. The high affinity of FP3 for both TGF-β isoforms and the substantial potency of FP3 in two TGF-β neutralization assays suggests that the TGF-β-binding sequence may be partially masked in intact $\alpha_2$M. Like TGF-β1 and TGF-β2, NGF-β bound to dissociated $\alpha_2$M subunits, suggesting that intact quaternary structure and the resulting $\alpha_2$M central cavity or trap is not necessary.

EXAMPLE 2
Identification of a Peptide Fragment FP3' that Binds TGF-β

The C-terminal region of FP3 was expressed as a GST-$\alpha_2$M fusion protein according to the following procedure and designated FP3'. The cDNA encoding amino acids 700–800 from human $\alpha_2$M was generated by PCR using the primers: 5'TGGCCTTAAGTGTGAAGGCCTCTCCACG3' SEQ ID NO:5 and 5'GCATGGATCCGAAGGTCTACGTGTAGGT3' SEQ ID NO:6 and the $\alpha_2$M cDNA as a template. The PCR fragment was isolated and ligated in pCRII. The fragment encoding amino acids 700–800 was excised by digestion with the restriction endonucleases BamHI and Eco RI, and cloned into pGEX2T. Expression of the FP3' was induced with IPTG (0.1 mM). A highly pure preparation of FP3' was obtained by following the purification procedure described for isolating for FP3 (see Example 1).

---

What is claimed is:

1. A substantially pure peptide fragment of α$_2$-macroglobulin, said peptide fragment consisting of the sequence of SEQ ID NO: 2 or a fragment of SEQ ID NO: 2, wherein said peptide fragment retains the ability to bind to TGF-β.

2. A substantially pure peptide wherein the peptide is SEQ ID NO: 2.

3. A composition for inhibiting TGF-β activity, said composition comprising a peptide fragment of α$_2$-macroglobulin and a pharmaceutically acceptable carrier, wherein said peptide fragment binds to TGF-β and consists of the amino acid sequence of SEQ ID NO: 2, or a fragment of SEQ ID NO: 2.

4. The composition of claim 3 wherein said peptide fragment of α$_2$-macroglobulin is a 10 amino acid fragment of the sequence of SEQ ID NO: 2.

5. The composition of claim 3 wherein said peptide fragment of α$_2$-macroglobulin is the amino acid sequence of SEQ ID NO: 2.

* * * * *